US00PP22963P3

(12) United States Plant Patent
de Bruijn

(10) Patent No.: US PP22,963 P3
(45) Date of Patent: Aug. 14, 2012

(54) BERMUDA GRASS PLANT NAMED 'BARAZUR'

(50) Latin Name: ***Cynodon dactylon* (L.) Persoon**
Varietal Denomination: BARAZUR

(75) Inventor: Jacobus de Bruijn, Montech (FR)

(73) Assignee: Barenbrug USA, Inc., Tangent, OR (US)

( * ) Notice: Subject to any disclaimer, the term of this patent is extended or adjusted under 35 U.S.C. 154(b) by 0 days.

(21) Appl. No.: 12/661,307

(22) Filed: Mar. 15, 2010

(65) Prior Publication Data

US 2011/0225694 P1 Sep. 15, 2011

(51) Int. Cl.
*A01H 5/00* (2006.01)

(52) U.S. Cl. ..... Plt./389
(58) Field of Classification Search ..... Plt./389
See application file for complete search history.

(56) References Cited

OTHER PUBLICATIONS

Upov Plant Variety Database 2011/02 p. 1a and p. 1b search for cultivar BAR 1CD3.*

* cited by examiner

*Primary Examiner* — Annette Para
(74) *Attorney, Agent, or Firm* — Jondle & Associates, P.C.

(57) ABSTRACT

This invention relates to a new and distinct variety of Bermuda grass plant named 'BARAZUR', which is primarily characterized by rapid lateral spread that forms a dense sod, minimal thatch, and minimal vertical growth that requires very little mowing, and producing very few seed heads, if any, is disclosed.

2 Drawing Sheets

Genus and species: *Cynodon dactylon* (L.) Persoon.
Variety denomination: 'BARAZUR'.

BACKGROUND OF THE NEW PLANT

The present invention relates to a new and distinct Bermuda grass plant designated 'BARAZUR' and botanically known as *Cynodon dactylon* (L.) Persoon. This new Bermuda grass was developed from research germplasm collections near Sydney, Australia in 1997. Germplasm selected from the 1997 evaluation was then evaluated in turf plots in southern France from 1998 to 1999. The most promising germplasm was selected and designated 'BARAZUR', which is also known as 'BAR 1CD3'. 'BARAZUR' was then sent to Virginia for further evaluation and selection. A selection was made in 2000 in Virginia for its turf quality. The present invention has been found to be stable and reproduce true to type through successive asexual propagations.

Plant Breeder's Rights for this plant were applied for in The Netherlands and Community Plant Variety Rights in Europe in 2001 and granted in 2003 and 2004 respectively; both were withdrawn in 2006. Both applications were given the title 'BARAZUR'. 'BARAZUR' has not been made publicly available more than one year prior to filing of this application.

SUMMARY OF THE INVENTION

The following are the most outstanding and distinguishing characteristics of this new cultivar when grown under normal horticultural practices in Raleigh, N.C., Savelletri di Fasano, Italy, Las Cruces, N. Mex., and Wharton, Tex.

1. Rapid lateral spread that forms a dense sod;
2. Minimal thatch;

3. Minimal vertical growth that requires very little mowing; and
4. Very low number of inflorescences (seed heads) produced.

DESCRIPTION OF THE PHOTOGRAPH AND FIGURE

This new Bermuda grass plant is illustrated by the accompanying photograph taken in Wharton, Tex., on May 6, 2009.

DESCRIPTION OF THE NEW VARIETY

Figure 1:
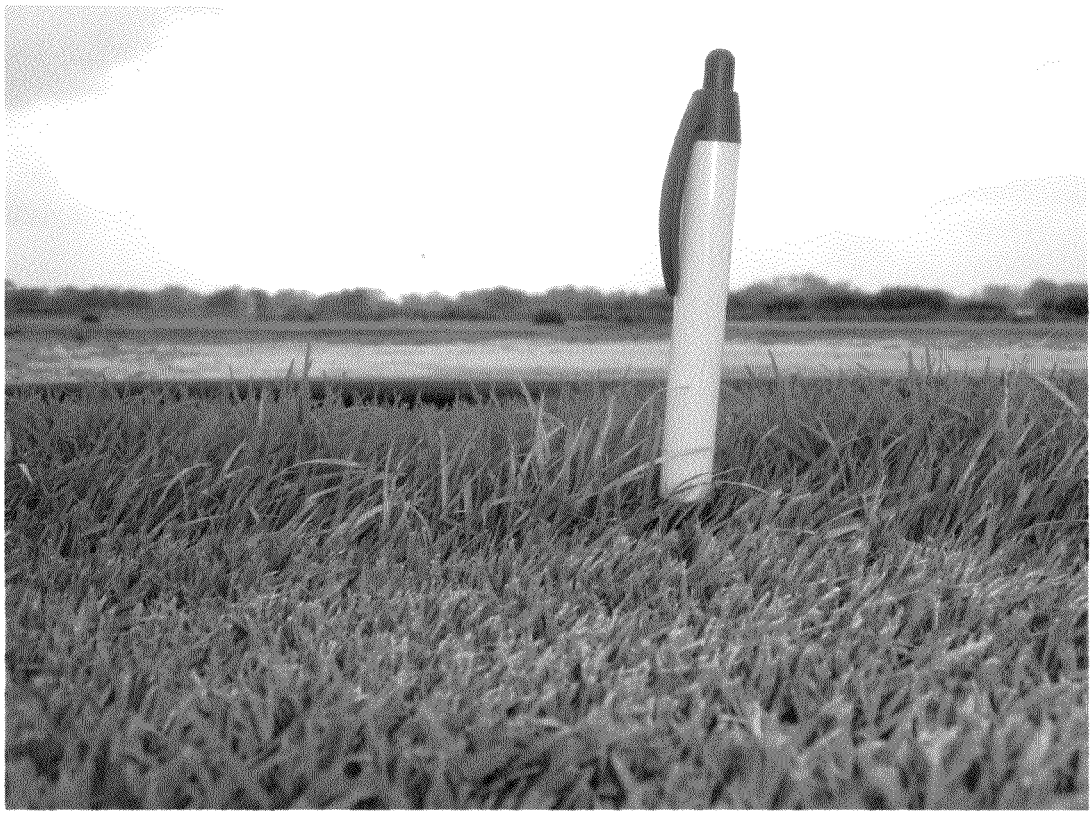
FIG. 1 shows a photo of the invention 30 days after mowing.

The following description of 'BARAZUR' is based on observations taken during the 2003 to 2009 growing seasons in Raleigh, N.C., Savelletri di Fasano, Italy, Las Cruces, N. Mex., and Wharton, Tex. Color references are primarily to The R.H.S. Colour Chart of The Royal Horticultural Society of London (R.H.S.), Fifth Edition (2007).

DETAILED BOTANICAL DESCRIPTION

Classification:
*Family*.—Poaceae.
*Botanical*.—*Cynodon dactylon* (L.) Persoon.
*Common name*.—Bermuda grass.
*Variety name*.—'BARAZUR'.

Shoot:
*Density* ($cm^{-2}$).—7.3 to 7.4.

Root:
*Rhizome and shoot density* ($cm\ cm^{-2}$).—4.4 to 4.5.

Internode:

*Length* (*cm*).—0.9 to 1.1.

*Diameter* (*mm*).—1.5 to 1.6.

Blade:

*Leaf blade width* (*mm*).—1.6 to 1.8.

*Color of leaf blade* (*both upper and lower surfaces*).—RHS N137D.

Flower stalk:

*Color*.—RHS 144A.

Table 1 shows a visual assessment and comparison of 'BARAZUR' with several commercially available Bermuda grass varieties conducted in Savelletri di Fasano, Italy between 2003 and 2006. The experimental design was a randomized block with four replications. Plot size was 3 m×2 m (0.5 m alleyways between plots). Planting date was Aug. 8, 2003 by sprigging (sprigs in rows) or seeding (1.5 kg 100 $m^2$ seed rate). Mowing height of the plot was 30 mm from 2003 to 2005 and 18 mm from 2006 on. The fertilization of the plot included 3.0 kg 100 $m^{-2}$ nitrogen per growing season (April to October) and 2.5 kg 100 $m^{-2}$ potassium per growing season (April to October). Column one shows the cultivar name, column two shows the propagule type (seeded/vegetative), column three shows the percentage of ground cover during establishment of the grass as of Oct. 11, 2003, column four shows the percent green color and the fall color retention on Dec. 3, 2003, column five shows the spring greenup by percent green color on Mar. 14, 2004, column six shows the spring greenup by percent green color on Apr. 15, 2004, column seven shows the spring greenup by percent green color on May 25, 2004 and row fourteen shows the LSD with an alpha of 0.05.

TABLE 1

Visual Assessment: Percent Ground Cover During Establishment, Fall Color Retention (2003) and Spring Greenup (2004).

| Cultivar | Propagule Type | Percent Ground Cover Oct. 11, 2003 | Fall Color Retention Dec. 3, 2003 | Percent Green Color Spring Greenup - 2004 Mar. 14, 2004 | Apr. 15, 2004 | May 25, 2004 |
|---|---|---|---|---|---|---|
| Common | seeded | 100 | 90 | 15 | 61 | 100 |
| Princess 77 | seeded | 99 | 91 | 55 | 89 | 100 |
| Riviera | seeded | 100 | 89 | 56 | 89 | 100 |
| Yukon | seeded | 88 | 39 | 20 | 91 | 100 |
| Tifway 419 | vegetative | 69 | 91 | 70 | 95 | 100 |
| Tifdwarf | vegetative | 30 | 90 | 10 | 38 | 84 |
| Santa Ana | vegetative | 71 | 92 | 65 | 95 | 100 |
| Tiftsport | vegetative | 33 | 91 | 60 | 83 | 99 |
| 'BARAZUR' | vegetative | 40 | 68 | 50 | 66 | 95 |
| LSD (P = 0.05) | | 21 | 6 | 6 | 19 | 12 |

Table 2 below shows a visual assessment and comparison of 'BARAZUR' with several commercially available Bermuda grass varieties. The comparison was made in the spring of 2006 in Savelletri di Fasano, Italy between 2003 and 2006. The experimental design was a randomized block with four replications. Plot size was 3 m×2 m (0.5 m alleyways between plots). Planting date was Aug. 8, 2003 by sprigging (sprigs in rows) or seeding (1.5 kg 100 $m^2$ seed rate). Mowing height of the plot was 30 mm from 2003 to 2005 and 18 mm from 2006 on. The fertilization of the plot included 3.0 kg 100 $m^{-2}$ nitrogen per growing season (April to October) and 2.5 kg 100 $m^{-2}$ potassium per growing season (April to October). Column one shows the cultivar name, column two shows the percent green color on Mar. 2, 2006, column three shows the percent green color on Mar. 15, 2006, column four shows the percent green color on Mar. 30, 2006, and row thirteen shows the LSD with an alpha of 0.05

TABLE 2

Spring Greenup 2006

| Cultivar | Percent Green Color Mar. 2, 2006 | Mar. 15, 2006 | Mar. 30, 2006 |
|---|---|---|---|
| Common | 0 | 5 | 61 |
| Princess | 0 | 0 | 60 |
| Riviera | 0 | 10 | 79 |
| Yukon | 0 | 6 | 75 |
| Tifway 419 | 1 | 8 | 84 |
| Tifdwarf | 0 | 0 | 63 |
| Santa Ana | 0 | 9 | 78 |
| Tifsport | 0 | 0 | 74 |
| 'BARAZUR' | 0 | 0 | 74 |
| LSD (P = 0.05) | 2 | 4 | 10 |

Table 3 below shows a visual assessment and comparison of 'BARAZUR' with several commercially available Bermuda grass varieties. The comparison was made in the fall of 2004, 2005, and 2006 in Savelletri di Fasano, Italy between 2003 and 2006. The experimental design was a randomized block with four replications. Plot size was 3 m×2 m (0.5 m alleyways between plots). Planting date was Aug. 8, 2003 by sprigging (sprigs in rows) or seeding (1.5 kg 100 $m^2$ seed rate). Mowing height of the plot was 30 mm from 2003 to 2005 and 18 mm from 2006 on. The fertilization of the plot included 3.0 kg 100 $m^{-2}$ nitrogen per growing season (April to October) and 2.5 kg 100 $m^{-2}$ potassium per growing season (April to October). Column one shows the cultivar name, column two shows the turf quality (9=best and 1=poorest) on Sep. 23, 2004, column three shows the turf quality (9=best and 1=poorest) on Sep. 29, 2005, column four shows the turf color on Sep. 23, 2004 (9=dark green and 1=light green), and row thirteen shows the LSD with an alpha of 0.05.

TABLE 3

Visual Assessment: Turf Quality and Turf Color

| Cultivar | Turf Quality (9 = best, 1 = poorest) Sep. 23, 2004 | Sep. 29, 2005 | Color (9 = dark green, 1 = light green) Sep. 23, 2004 |
|---|---|---|---|
| Common | 5.4 | 4.0 | 5.3 |
| Princess 77 | 7.1 | 6.0 | 7.0 |
| Riviera | 6.8 | 4.8 | 6.8 |
| Yukon | 7.3 | 5.5 | 6.8 |
| Tifway 419 | 7.8 | 5.8 | 7.6 |
| Tifdwarf | 7.8 | 7.0 | 7.8 |
| Santa Ana | 7.5 | 6.0 | 7.5 |
| Tifsport | 7.8 | 6.1 | 8.0 |
| 'BARAZUR' | 8.3 | 7.3 | 8.4 |
| LSD (P = 0.05) | 0.4 | 0.5 | 0.4 |

Table 4 below shows a comparison of morphologicl characteristics recorded in 2004. The comparison was made in Savelletri di Fasano, Italy between 2003 and 2006. The experimental design was a randomized block with four replications. Plot size was 3 m×2 m (0.5 m alleyways between plots). Planting date was Aug. 8, 2003 by sprigging (sprigs in rows) or seeding (1.5 kg 100 $m^2$ seed rate). Mowing height of the plot was 30 mm from 2003 to 2005 and 18 mm from 2006 on. The fertilization of the plot included 3.0 kg 100 $m^{-2}$ nitrogen per growing season (April to October) and 2.5 kg 100 $m^{-2}$ potassium per growing season (April to October). Column one shows the cultivar name, column two shows the shoot density ($cm^{-2}$) (one 70 mm core sample per plot), column three shows the rhizome and stolon density (cm $cm^{-2}$) (one 70 mm core sample per plot), column four shows the internode length (cm) (20 internodes were measured per plot), column five shows the internode diameter (mm) (20 internodes were measured per plot), column six shows the leaf blade width (mm) (20 fully expanded leaves were measured per plot), and row twelve shows the LSD with an alpha of 0.05.

TABLE 4

Comparative Turfgrass Morphological Characteristics Recorded in 2004

| Cultivar | Shoot Density ($cm^{-2}$) | Rhizome and Stolon Density (cm $cm^{-2}$) | Internode Length (cm) | Internode Diameter (mm) | Leaf Blade Width (mm) |
|---|---|---|---|---|---|
| Common | 3.6 | 0.4 | 1.4 | 1.3 | 1.5 |
| Princess 77 | 6.6 | 0.8 | 1.2 | 0.9 | 1.4 |
| Riviera | 6.7 | 0.9 | 1.4 | 1.3 | 1.3 |
| Yukon | 5.1 | 1.0 | 1.3 | 1.3 | 1.4 |
| Tifway 419 | 5.9 | 1.1 | 1.5 | 1.5 | 1.3 |
| Tifdwarf | 9.4 | 2.2 | 1.2 | 1.3 | 1.2 |
| Santa Ana | 8.2 | 3.0 | 1.5 | 1.4 | 1.1 |
| Tifsport | 11.2 | 2.7 | 1.8 | 1.4 | 1.2 |
| 'BARAZUR' | 7.3 | 4.5 | 1.1 | 1.6 | 1.8 |
| LSD (P = 0.05) | 2.7 | 1.8 | 0.3 | 0.4 | 0.2 |

Table 5 below shows a comparison of morphological characteristics recorded in 2005. The comparison was made in Savelletri di Fasano, Italy between 2003 and 2006. The experimental design was a randomized block with four replications. Plot size was 3 m×2 m (0.5 m alleyways between plots). Planting date was Aug. 8, 2003 by sprigging (sprigs in rows) or seeding (1.5 kg 100 $m^2$ seed rate). Mowing height of the plot was 30 mm from 2003 to 2005 and 18 mm from 2006 on. The fertilization of the plot included 3.0 kg 100 $m^{-2}$ nitrogen per growing season (April to October) and 2.5 kg 100 $m^{-2}$ potassium per growing season (April to October). Column one shows the cultivar name, column two shows the shoot density ($cm^{-2}$)(one 70 mm core sample per plot), column three shows the rhizome and stolon density (cm $cm^{-2}$) (one 70 mm core sample per plot), column four shows the internode length (cm) (20 internodes were measured per plot), column five shows the internode diameter (mm) (20 internodes were measured per plot), column six shows the leaf blade width (mm) (20 fully expanded leaves were measured per plot), and row twelve shows the LSD with an alpha of 0.05.

TABLE 5

Comparative Turfgrass Morphological Characteristics Recorded In 2005

| Cultivar | Shoot Density ($cm^{-2}$) | Rhizome and Stolon Density (cm $cm^{-2}$) | Internode Length (cm) | Internode Diameter (mm) | Leaf Blade Width (mm) |
|---|---|---|---|---|---|
| Common | 3.7 | 0.2 | 1.3 | 1.7 | 1.8 |
| Princess 77 | 9.7 | 0.7 | 1.2 | 0.7 | 1.4 |
| Riviera | 5.4 | 0.4 | 1.0 | 1.1 | 1.4 |
| Yukon | 6.0 | 0.9 | 1.7 | 1.5 | 1.7 |
| Tifway 419 | 5.6 | 1.6 | 1.2 | 1.6 | 1.4 |

TABLE 5-continued

Comparative Turfgrass Morphological Characteristics Recorded In 2005

| Cultivar | Shoot Density ($cm^{-2}$) | Rhizome and Stolon Density (cm $cm^{-2}$) | Internode Length (cm) | Internode Diameter (mm) | Leaf Blade Width (mm) |
|---|---|---|---|---|---|
| Tifdwarf | 10.5 | 2.7 | 1.1 | 1.1 | 1.2 |
| Santa Ana | 13.1 | 2.9 | 1.2 | 1.5 | 1.0 |
| 'BARAZUR' | 7.4 | 4.4 | 0.9 | 1.5 | 1.6 |
| Tifsport | 12.8 | 2.8 | 1.4 | 1.4 | 1.1 |
| LSD (P = 0.05) | 3.8 | 1.1 | 0.8 | 0.4 | 0.1 |

Table 6 shows the average plant heights (cm) after 56 days and 77 days without mowing the plots on May 6, 2009 and May 27, 2009. The date of planting was Jun. 13, 2008 in Wharton, Tex. Column one shows the cultivar name, column two shows the plant height after 56 days (cm), column three shows the plant height after 77 days (cm), and row ten shows the LSD with an alpha of 0.05. The statistical analysis is based on eight observations per plot. All varieties in Table 6 are vegetatively propagated.

TABLE 6

Average Plant Height (cm) After 56 Days And 77 Days Without Mowing The Plots. Planting Date Jun. 13, 2008

| Cultivar | 56 days May 6, 2009 (cm) | 77 days May 27, 2009 (cm) |
|---|---|---|
| 'BARAZUR' | 6.91 | 14.61 |
| Tifton 419 | 10.72 | 17.70 |
| Plateau | 12.86 | 17.86 |
| Patriot | 14.84 | 23.81 |
| Celebration | 16.59 | 31.91 |
| LSD (P = 0.05) | 1.05 | 1.39 |

Table 7 shows a comparison of the genetic color, leaf texture, and number of seed heads. Data was collected from plots planted in the summer of 2007 in Raleigh, N.C. Column one shows the cultivar name, column two shows the propagule type, column three shows the genetic color on Sep. 19, 2007 with (9=dark green and 1=light green), column four shows the genetic color on Oct. 5, 2007 with (9=dark green and 1=light green), column five shows the genetic color in September, 2008 with (9=dark green and 1=light green), column six shows the leaf texture on Oct. 5, 2007 with a score of nine (9) equaling the finest texture, column seven shows the leaf texture in September, 2008 with a score of nine (9) equaling the finest texture, column eight shows the number of seed heads on Oct. 7, 2007 with a score of nine (9) equaling no seed heads produced and one (1) equaling the highest number of seed heads produced, column nine shows the number of seed heads on Jul. 21, 2008 with a score of nine (9) equaling no seed heads produced and one (1) equaling the highest number of seed heads produced, column ten shows the number of seed heads in Oct. 26, 2008 with a score of nine (9) equaling no seed heads were produced and one (1) equaling the highest number of seed heads produced, and column eleven shows the average number of seeds heads for 2007 and 2008, with a score of nine (9) equaling no seed heads were produced and one (1) equaling the highest number of seed heads produced. Rows 14 through 16 show the statistical analyses of the data in Table 7, including the LSD with an alpha of 0.05, the standard deviation, and Coefficient of Variation (CV).

TABLE 7

Shows a Comparison of the Average Genetic Color, Leaf Texture and Number of Seed Heads in 2007 and 2008

| | | Genetic Color (9 = darkest green) | | | Leaf Texture (9 = finest texture) | |
|---|---|---|---|---|---|---|
| Entry | Propagule Type | Sep. 19, 2007 | Oct. 5, 2007 | Sep. of 2008 | Oct. 5, 2007 | Sep. of 2008 |
| 'BARAZUR' | vegetative | 8.3 | 8.0 | 8.0 | 9.0 | 9.0 |
| Riviera | seeded | 6.0 | 5.7 | 6.3 | 7.0 | 6.7 |
| Princess 77 | seeded | 7.0 | 6.3 | 7.0 | 7.7 | 7.3 |
| Midlawn | vegetative | 7.0 | 6.3 | 6.0 | 7.3 | 9.0 |
| Tifway | vegetative | 8.0 | 7.3 | 8.0 | 8.3 | 9.0 |
| Premier | vegetative | 8.3 | 7.0 | 7.7 | 9.0 | 8.7 |
| Sunsport | seeded | 6.3 | 5.0 | 5.3 | 6.7 | 5.3 |
| Patriot | vegetative | 9.0 | 8.0 | 8.3 | 8:0 | 8.3 |
| Yukon | seeded | 6.7 | 6.3 | 7.3 | 6.7 | 6.7 |
| Tifton 11 | vegetative | 8.3 | 7.3 | 7.3 | 7.7 | 7.3 |
| LSD (P = 0.05) | | 0.8 | 1.2 | 0.9 | 0.8 | 1.1 |
| Standard Deviation | | 0.5 | 0.7 | 0.5 | 0.5 | 0.7 |
| CV | | 7.13 | 11.28 | 8.1 | 6.73 | 10.1 |

| | | Number of Seed Heads (9 = no seed heads) | | | Average |
|---|---|---|---|---|---|
| Entry | Propagule Type | Oct. 7, 2007 | Jul. 21, 2008 | Oct. 26, 2008 | Number of Seed Heads 2007-2008 |
| 'BARAZUR' | vegetative | 8.7 | 9.0 | 9.0 | 8.9 |
| Riviera | seeded | 7.7 | 6.7 | 7.7 | 7.3 |
| Princess 77 | seeded | 5.7 | 4.0 | 6.0 | 5.2 |
| Midlawn | vegetative | 8.3 | 7.3 | 9.0 | 8.2 |
| Tifway | vegetative | 8.3 | 7.0 | 9.0 | 8.1 |
| Premier | vegetative | 8.0 | 8.7 | 8.7 | 8.4 |
| Sunsport | seeded | 4.0 | 3.3 | 5.7 | 4.3 |
| Patriot | vegetative | 7.3 | 9.0 | 6.7 | 7.7 |
| Yukon | seeded | 7.7 | 5.7 | 8.0 | 7.1 |
| Tifton 11 | vegetative | 8.7 | 8.3 | 9.0 | 8.7 |
| LSD (P = 0.05) | | 1.1 | 1.1 | 1.5 | 0.8 |
| Standard Deviation | | 0.7 | 0.7 | 0.9 | 0.5 |
| CV | | 10.47 | 12 | 13.17 | 7.44 |

Table 8 shows a non-replicated comparison of turf quality and genetic color. Data was collected in the summer and fall of 2008 from plots planted on Jun. 13, 2008 in Wharton, Tex. Column one shows the cultivar name, column two shows the turf quality (9=best and 1=poorest) on Jul. 11, 2008, column three shows the turf quality (9=best and 1=poorest) on Jul. 22, 2008, column four shows the turf quality (9=best and 1=poorest) on Aug. 29, 2008, column five column the turf quality (9=best and 1=poorest) on Sep. 19, 2008, column six shows the turf quality (9=best and 1=poorest) on Oct. 2, 2008, column seven shows the average turf quality, column eight shows the genetic color on Jul. 11, 2008 (9=dark green and 1=light green), column nine shows the genetic color on Jul. 22, 2008 (9=dark green and 1=light green), column ten shows the genetic color on Aug. 29, 2008 (9=dark green and 1=light green), column eleven shows the genetic color on Sep. 19, 2008 (9=dark green and 1=light green), column twelve shows the genetic color on Oct. 2, 2008 (9=dark green and 1=light green), and column thirteen shows the average genetic color.

TABLE 8

Comparison of Turf Quality and Genetic Color
Data is from Wharton, Texas. Planting date: Jun. 13, 2008

| | Turf Quality (9 = best turf quality) | | | | | |
|---|---|---|---|---|---|---|
| Cultivar | Jul. 11, 2008 | Jul. 22, 2008 | Aug. 29, 2008 | Sep. 19, 2008 | Oct. 2, 2008 | Average |
| Plateau | 7 | 7 | 7 | 7 | 7 | 7.0 |
| Patriot | 7 | 7 | 5 | 6 | 5 | 6.0 |
| 'BARAZUR' | 7 | 7 | 8 | 7 | 6 | 7.0 |
| Celebration | 7 | 7 | 6 | 6 | 6 | 6.4 |
| Tifton 419 | 7 | 7 | 7 | 6 | 6 | 6.6 |

| | Genetic Color (9 = dark green) | | | | | |
|---|---|---|---|---|---|---|
| Cultivar | Jul. 11, 2008 | Jul. 22, 2008 | Aug. 29, 2008 | Sep. 19, 2008 | Oct. 2, 2008 | Average |
| Plateau | 7 | 8 | 8 | 8 | 7.6 | 7.7 |
| Patriot | 6 | 6 | 7 | 6 | 6.2 | 6.2 |
| 'BARAZUR' | 7 | 8 | 8 | 7 | 7.4 | 7.5 |
| Celebration | 7 | 7 | 7 | 8 | 7.1 | 7.2 |
| Tifton 419 | 6 | 6 | 6 | 6 | 6.1 | 6.0 |

Table 9 shows a comparison of the number of seed heads produced and percent ground cover. Data was collected in the summer and fall of 2008 from plots planted on Jun. 13, 2008 in Wharton, Tex. Column one shows the cultivar name, column two shows the seed head number on Jul. 11, 2008 with a score of nine (9) equaling the highest number of seed heads produced, column three shows the seed head number on Jul. 22, 2008 with a score of nine (9) equaling the highest number of seed heads produced, column four shows the seed head number on Aug. 29, 2008 with a score of nine (9) equaling the highest number of seed heads produced, column five shows the seed head number on Sep. 19, 2008 with a score of nine (9) equaling the highest number of seed heads produced, column six shows the seed head number on Oct. 2, 2008 with a score of nine (9) equaling the highest number of seed heads produced, column seven shows the average number of seed head produced, column eight shows the percent ground cover on Jul. 11, 2008, column nine shows the percent ground cover on Jul. 22, 2008, column ten shows the percent ground cover on Aug. 29, 2008, column eleven shows the percent ground cover on Sep. 19, 2008, and column twelve shows the percent ground cover on Oct. 2, 2008.

TABLE 9

Comparison of Seed Head Production and Percent Ground Cover
Data is from Wharton, Texas. Planting date: Jun. 13, 2008

| | Seed Head Number (9 = highest number of seed heads produced) | | | | | |
|---|---|---|---|---|---|---|
| Cultivar | Jul. 11, 2008 | Jul. 22, 2008 | Aug. 29, 2008 | Sep. 19, 2008 | Oct. 2, 2008 | Average |
| Plateau | 0 | 0 | 3 | 3 | 3 | 1.8 |
| Patriot | 0 | 0 | 0 | 0 | 9 | 1.8 |
| 'BARAZUR' | 0 | 0 | 0 | 0 | 0 | 0.0 |
| Celebration | 0 | 0 | 0 | 0 | 0 | 0.0 |
| Tifton 419 | 0 | 0 | 0 | 0 | 0 | 0.0 |

TABLE 9-continued

Comparison of Seed Head Production and Percent Ground Cover
Data is from Wharton, Texas. Planting date: Jun. 13, 2008

| | Percent Ground Cover | | | | |
|---|---|---|---|---|---|
| Cultivar | Jul. 11, 2008 | Jul. 22, 2008 | Aug. 29, 2008 | Sep. 19, 2008 | Oct. 2, 2008 |
| Plateau | 35 | 75 | 100 | 100 | 100 |
| Patriot | 90 | 100 | 100 | 100 | 100 |
| 'BARAZUR' | 65 | 90 | 100 | 100 | 100 |
| Celebration | 70 | 95 | 100 | 100 | 100 |
| Tifton 419 | 50 | 85 | 100 | 100 | 100 |

Table 10 shows a written comparison of various Bermuda grass varieties when compared with 'BARAZUR'. Data is from Wharton, Tex., with a planting date of Jun. 13, 2008. As shown in Table 10, 'BARAZUR' is distinguished from other Bermuda grass varieties by its blue green color, very low vertical growth, tight and dense growth, short leaf, little or no scalping when mowed, and no seed head production.

TABLE 10

Comparison of Characteristics of Various Bermuda Grass Varieties

| | |
|---|---|
| Plateau | Blue green color; low vertical growth; tight and dense; short leaf; little or no scalping when mowed; some seed heads produced. |
| Patriot | Yellow green color; tall vertical growth; thin in turf; course leaf; scalped when mowed; numerous seed heads produced. |
| 'BARAZUR' | Blue green color; very low vertical growth; tight and dense; short leaf; little or no scalping when mowed; no seed heads produced. |
| Celebration | Blue green color; medium vertical growth; thin; coarse leaf |
| Tifton 419 | Light green in color; tall growth; thin, fine leaf blades, scalping when mowed. |

An analysis of the genetic relationship between 'BARAZUR' and various Bermuda grass samples was conducted in the fall of 2009. Amplified Fragment Length Polymorphism (AFLP) markers were used in the analysis. From each DNA-sample, three independent EcoRI/MseI pre-amplifications were prepared. This rendered a total of eighteen pre-amplifications for analysis and allowed a check of the reproducibility of the AFLP-protocol when the same DNA-sample was used repeatedly for analysis. For each pre-amplification, eight AFLP primer combinations were used. Six primer combinations were used as taught by Wu et al., *Genome* 47:689-696 (2004) and are shown in Table 11. Primer combination e-GCTG/m-CAG, as taught by Wu et al. (2004) was replaced by the primer combination e-ACA/m-CAG to avoid the necessity to carry out two preamplifications for each sample in triplicate. Primer combination e-AGT/m-CAG was replaced by primer combination e-ACA/m-CAT, to avoid unnecessary delay in the completion of the analysis. An ABI Prism 3130×1 capillary sequencer was used for the AFLP-fragment separation and detection. GeneScan 500 Rox labelled size standard was loaded in each run to allow fragment sizing. The fluorescent AFLP fingerprints were scored using Genemapper v. 3.7 (Applied Biosystems) and the presence or absence of each marker in each sample was recorded. As shown in Table 12, the presence or absence of each marker was used to construct a scoring table where a score of 1 equalled presence and a score of 0 equalled absence for data analysis. Genetic similarity between pairs of samples was estimated using the percentage of shared AFLP bands. This coefficient varies between 0 (complete dissimilarity) and 1 (complete similarity). Calculations were carried out in STATISTICA v8.0 (Stat Soft Inc., Tulsa, Okla., USA).

TABLE 11

Restriction Enzymes and Selective Nucleotides Used,
Primer Combinations as cited by Wu et al. (2004)

| EcoRI MseI |
|---|
| PC1* ACT CAG |
| PC2* AAC CAG |
| PC3 ACA CAG |
| PC4* ACT CAT |
| PC5* AAC CAT |
| PC6* ACT CAC |
| PC7* AAC CAC |
| PC8 ACA CAT |

As shown in Table 11, eight primer combinations were used. These eight primer combinations rendered 373 polymorphic AFLP-bands for analysis. The fingerprints generated for replicated samples were compared. In most cases three repetitions were available for analysis for a given primer combination. Only a few differences were encountered when replicated samples were compared: for Patriot only one AFLP-band (PC8_al7) was not consistent among the three replications. For 'BARAZUR' only the AFLP-band PC3_al35 was not consistent among the three replications and for Tifway 419 only the AFLP-band PC7_al35 was not consistent. For Tifdwarf, Celebration, TifEagle and 'P-18' the replicates were identical. This demonstrated a high reliability of the results obtained.

As shown in Table 12, the analysis shows that the Bermuda grass varieties Tifdwarf, TifEagle and 'P-18' display an extremely high degree of similarity. No single polymorphism was detected between samples Tifdwarf and TifEagle among the 373 AFLP-bands screened. One single polymorphism (for band PC6_al29) was found between Tifdwarf and TifEagle, on the one side, and 'P-18' on the other side.

Figure 2:
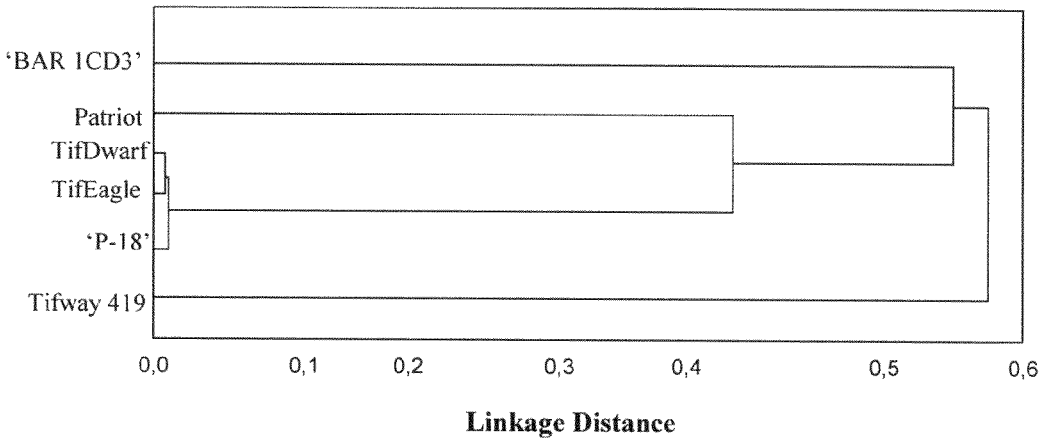
FIG. 2 shows a tree diagram of the genetic linkage distance of 'BARAZUR' with five other Bermuda grass cultivars.

The genetic relationships among the Bermuda grass samples tested have also been represented using Unweighted Pair Group Method with Arithmetic Mean clustering UPGMA (FIG. 2). As shown in FIG. 2, four clusters are evident with Tifway 419 being the most dissimilar, and TifDwarf, TifEagle, and 'P-18' being the most similar of the group.

TABLE 12

Analysis of the Genetic Similarity of Bermuda Grass Varieties

| | 'BARAZUR' | Patriot | TifDwarf | TifEagle | 'P-18' | Tifway 419 |
|---|---|---|---|---|---|---|
| 'BARAZUR' | 0.000 | 0.485 | 0.606 | 0.610 | 0.614 | 0.608 |
| Patriot | 0.485 | 0.000 | 0.408 | 0.412 | 0.416 | 0.535 |
| TifDwarf | 0.606 | 0.408 | 0.000 | 0.004 | 0.008 | 0.577 |
| TifEagle | 0.610 | 0.412 | 0.004 | 0.000 | 0.004 | 0.581 |
| 'P-18' | 0.614 | 0.416 | 0.008 | 0.004 | 0.000 | 0.581 |
| Tifway 419 | 0.608 | 0.535 | 0.577 | 0.581 | 0.581 | 0.000 |

I claim:

1. A new and distinct Bermuda grass plant as described and illustrated herein.

* * * * *

Tree Diagram Percent Disagreement Between Bermuda Grass Varieties